United States Patent [19]

Ohfune et al.

[11] 4,396,775
[45] Aug. 2, 1983

[54] HOMOSERINE ALDEHYDE DERIVATIVES FOR MUGINEIC ACIDS SYNTHESIS

[75] Inventors: Yasufumi Ohfune, Ibaraki; Masako Tomita, Takatsuki; Kyosuke Nomoto, Ibaraki, all of Japan

[73] Assignee: Suntory Limited, Osaka, Japan

[21] Appl. No.: 332,967

[22] Filed: Dec. 21, 1981

[30] Foreign Application Priority Data

Dec. 29, 1980 [JP] Japan .................................. 55-185538

[51] Int. Cl.³ .................. C07D 309/06; C07C 125/06; C07C 101/30
[52] U.S. Cl. ..................................... 549/419; 260/390; 260/239 A; 556/420; 556/419; 556/418; 560/27; 560/36; 560/160; 560/170; 562/568; 549/321
[58] Field of Search ....................... 260/345.8 R, 390; 549/419; 560/27, 36, 160, 170; 556/420, 419, 418

[56] References Cited
PUBLICATIONS

Ohfune et al., Chem. Lett., (6), 827–828, (1981).

*Primary Examiner*—Nicky Chan
*Attorney, Agent, or Firm*—Frishauf, Holtz, Goodman & Woodward

[57] ABSTRACT

This invention is related to homoserine aldehyde derivatives represented by the formula (I) which is important intermediate for producing mugineic acid, 2'-deoxymugineic acid, avenic acid A and homologue.

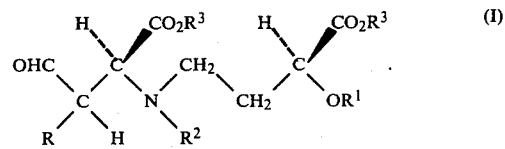

1 Claim, No Drawings

HOMOSERINE ALDEHYDE DERIVATIVES FOR MUGINEIC ACIDS SYNTHESIS

This invention is related to homoserine aldehyde derivatives represented by the formula (I) which is important intermediate for producing mugineic acid, 2′-deoxymugineic acid, avenic acid A and nomologue.

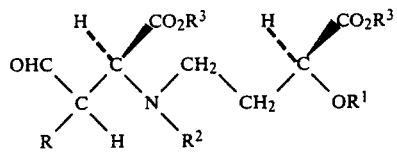

wherein R is hydrogen or hydroxy, $R^1$ is selected from a group consisting of tetrahydropyranyl, methoxymethylene, methoxyethoxymethylene, 1-ethoxyethyl, t-butyl, dimethyl-t-butylsilyl, acetyl, trifluoroacetyl, triphenylmethyl or diphenylmethyl, $R^2$ is selected from a group consisting of t-butoxycarbonyl, benzyloxycarbonyl, trifluoroacetyl or formyl and $R^3$ is selected from a group consisting of benzyl, p-methoxybenzyl, methyl, ethyl, or diphenylmethyl.

It is well-known that plants require many essential elements for their growth and maintenance; for example, iron is required in the biosynthesis of chlorophyll, and iron deficiency results in iron chlorosis. Recently several amino acids possessing chelating properties for iron and other metals have been isolated from the root washing of gramineous plants grown under iron-deficient conditions. Thus mugineic acid (II) has been isolated from barley (*Hordium vulgare L.*), 2′-deoxymugineic acid (III) from wheat (*Triticum aestivum L.*) and avenic acid A (IV) from oat (*Avena sativa L.*).

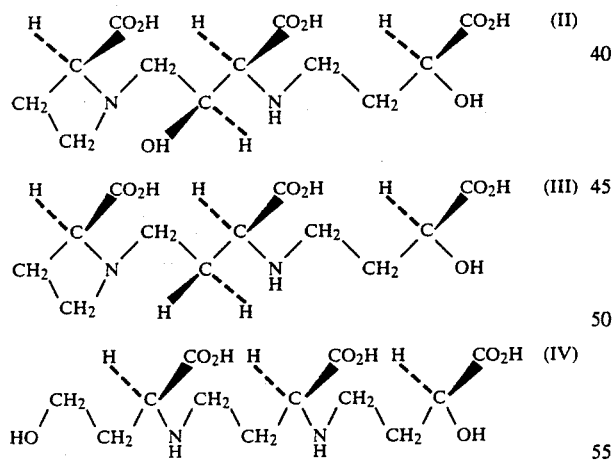

Hereinafter, we will call these compounds mugineic acids.

It was demonstrated that addition of either (II) or (III) to the medium of water-cultured rice at pH 7 increases the chlorophyll content, thus it is considered that they are involved in the uptake and transport of iron (and other elements) in higher plants.

Recently, it is well elucidated that mugineic acids possesses chelating activity with $Cu^{2+}$, $Co^{3+}$, etc. in spite of low molecular weight. Thus, these are the chelating agent with smallest molecular weight from natural source, and is expected for various utilities.

We succeeded in the total synthesis of mugineic acids and obtained some new important intermediates described below during the cource of this study.

The invention compounds are synthesized as follows.

Reaction of the α-hydroxy-γ-butyrolactone derivative (V) with $R^3X$ (X=halogen) in DMF-$H_2O$ in the presence (or absence) of crown-ether (for example, 18-crown-6) afforded the γ-hydroxybutylic acid derivative (VI), which was oxidized with pyridinium chlorochromate (PCC) to give the aldehyde (VII).

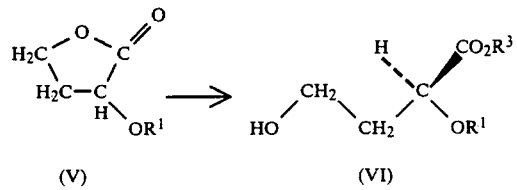

Coupling reaction of (VII) and α-amino-γ-butyrolactone trifluoroacetate (VIII) (or HCl, HBr) gave the N-substituted-α-amino-γ-butyrolactone derivative (IX).

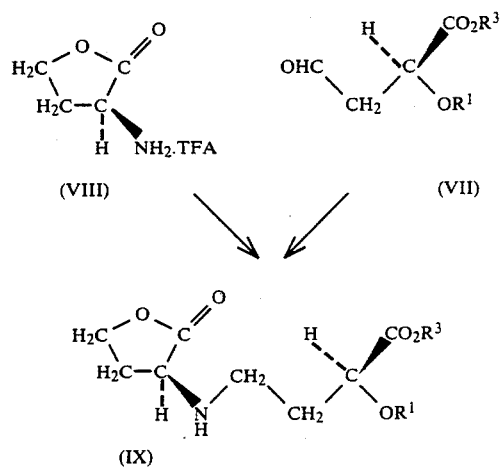

After protection of imino group with $R^2$ (X), γ-lactone unit was hydrolysed in the same manner (V→VI) to give the γ-hydroxybutyric acid derivative (XI).

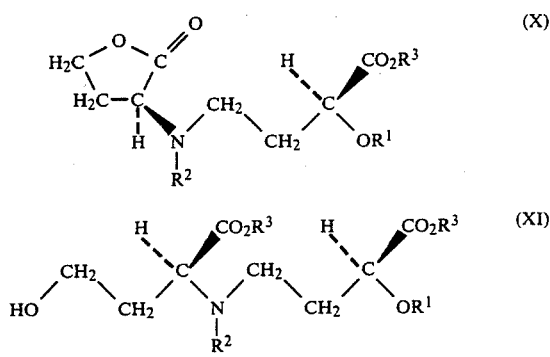

(XI) was converted into the homoserine aldehyde (I), one of invention compound (R=), with PCC oxidation. On the other hand, employment of the α-amino-β-hydroxy-γ-butyrolactone derivative (XII) instead of deoxy compound (VIII) gives another invention compound (I) (R=OH).

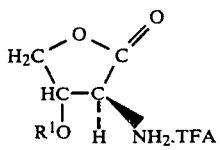

Transformations of the invention compound (I) to mugineic acid (II) and 2'-deoxymugineic acid (III) were achieved in the following.

Coupling reaction of (I) and azetizine-2-carboxylic acid trifluoroacetate (XIII) in methanol by means of $NaBH_3CN$ provided the mugineic acid (II) and 2'-deoxymugineic acid (III) derivatives in which hydroxy, imino and carboxyl groups were protected with $R^1$, $R^2$ and $R^3$ respectively. Then, carboxyl protecting group was removed by hydrogenation with $H_2/PtO_2$. Finally, both of imino and hydroxy protecting groups were removed with acidic treatment such as Trifluoroacetic acid.

On the other hand, Avenic acid A (IV) was obtained in the same manner by coupling of invention compound (I) (R=H) and trifluoroacetate of α-aminobutyric acid derivative (XIV) as described above. Alternative pathway to Avenic acid A from the invention compound (I) R=H) were also effective by means of α-amino-γ-butyrolactone trifluoroacetate derivative (VIII) instead of (XIV). Coupling product (XV) of (I) and (VIII) followed by deprotection in the same manner as before and subsequent hydrolysis gave Avenic acid A (IV).

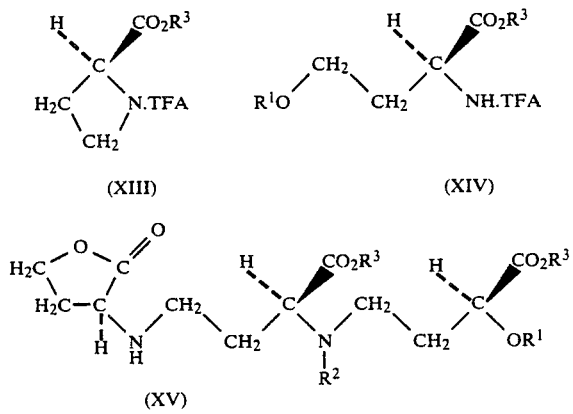

To avoid racemization, protection and deprotection of imino, hydroxyl and carboxyl groups are required mild reaction conditions during the synthesis of mugineic acids.

So it is required that the imino group is carbonylated such as $R^2$, the hydroxy groups are protected with $R^1$ and the carboxyl groups are esterified with $R^3$. As protecting groups for $R^1$, $R^2$, $R^3$, tetrahydropyranyl, t-butoxycarbonyl, and benzyl groups are respectively preferable.

The present invention will be described below in detail with reference to the following examples.

EXAMPLE 1

A solution of α-tetrahydroxypyranyl-γ-butyrolactone (425 mg, 2.28 mmole) in 2.5% KOH (6.0 ml, 2.28 mmole) and dioxane (6.0 ml) was allowed to stand for 14 hrs. under nitrogen at room temperature. The reaction mixture was distilled in vacuo and the resulting oily residue was dissolved with 10 ml of DMF and water (4:1). To above solution was added 469 mg (2.74 mmole) of benzyl bromide and 30 mg (0.164 mmole) of 18-crown-6. The reaction mixture was stirred for 5 hrs. poured into water and extracted with ether for three times (each 20 ml). The combined organic extracts were dried ($MgSO_4$), concentrated in vacuo and the resulting oily residue was chromatographed on Silic CC-7[50 g; elution with n-hexane: ether (1:1)] to give 537 mg (80%) of the γ-hydroxy-α-tetrahydropyranyloxybutyric acid benzyl ester (VI).

$IR(CHCl_3)$ 3450, 1735 $cm^{-1}$ $^1H$ $NMR(CDCl_3)$ δ7.35(S, 5H), 5.21(d, 1H, J=12 Hz), 5.14(d, 1H, J=12 Hz), 4.57(q, 1H, J=4.5, 9 Hz).

Analysis-Calculated for $C_{16}H_{22}O_5$(percent): C, 65.29; H, 7.53. Found: C, 64.88; H, 7.56.

To a suspension of 2.26 g (10.5 mmole) of PCC in dry methylene chloride (10 ml) was added at room temperature under $N_2$, a solution of the above compound. The reaction mixture was stirred for 2 hrs. and quenched by the addition of 60 ml of ether. The reaction mixture was suspended with powdered magnesium sulfate (10 g), filtered and concentrated in vacuo to give the oily residue.

Chromatography in Silic CC-7 eluted with ether-hexane (2:1) afforded 444 mg of the malic half aldehyde derivative, 3-formyl-2-tetrahydropyranoxypropionic acid benzyl ester (Yield; 76%) (VII).

$IR(CHCl_3)$ 1738, 1730 $cm^{-1}$ $^1H$ $NMR(CDCl_3)$ δ9.76(t, 1H, J=2 Hz), 7.34(s, 5H), 5.19(s, 2H), 4.84(t, 1H, J=8 Hz), 2.86(dd, 2H, J=2,8 Hz).

Analysis-Calculated for $C_{16}H_{20}O_5$(percent): C, 65.74; H, 6.90. Found: C, 65.49; H, 6.88.

To a solution of 930 mg (4.32 mmole) of β-amino-γ-butyrolactone trifluoroacetate in dry methanol (20 ml) at 0° C. was added a solution of the above compound (846 mg, 2.88 mmole) in methanol 15 ml and sodium cyanoborohydride (189 mg, 3.0 mmole). The reaction was warmed to room temperature after 30 minutes and allowed to stand for 14 hrs. The reaction mixture was poured into water and methanol was removed in vacuo. The resulting solution was extracted with chloroform. The organic extract was dried over with magnesium sulfate and concentrated in vacuo to give the oily residue, which was chromatographed on Silic CC-7 (elution with ether) yielded the α-tetrahydropyranoxy-γ-butyrolactoaminobutyric acid benzyl ester (977 mg) as a colorless oil (Yield: 80%) (IX).

$IR(CHCl_3)$ 3300, 1775, 1736 $cm^{-1}$ $^1H$ $NMR(CDCl_3)$ δ7.35(s, 5H), 5.20(d, 1H, J=12 Hz) 5.12(d, 1H, J=12 Hz), 4.50(t, 1H, J=7 Hz) Mass spectrum, m/e 292(M+—THP).

Analysis-Calculated for $C_{20}H_{27}O_6N$(percent): C, 63.64; H, 7.51; N, 3.71. Found: C, 63.21; H, 7.34;

A solution of the above compound (340 mg, 0.90 mmole), ditert-butyl di-carbonate (294 mg, 1.35 mmole) and triethylamine (4.5 mg, 0.045 mmole) in dry methylene chloride (5 ml) was stirred at room temperature for 20 hrs. The reaction mixture was concentrated in vacuo and chromatographed on Silica gel [elution with ether: hexane (4:1)] to give 387 mg of N-t-butoxycarbonyl-α-tetrahydropyranoxy-γ-butyrolactoaminobutyric acid benzyl ester as a colorless oil (Yield: 90%) (X).

$IR(CHCl_3)$, 1780, 1745, 1695 $cm^{-1}$ $^1H$ NMR ($CDCl_3$ at 50° C.) δ4.40(q, 1H, J=5, 8 Hz), 4.26(q, 1H, J=4, 9 Hz), 1.35(s, 9H).

Analysis-Calculated for $C_{25}H_{35}O_8N$(percent): C, 62.87; H, 7.39. Found: C, 62.81; H, 7.61.

A solution of the above compound (460 mg, 0.96 mmole) in 5.06 ml of KOH (1.92 mmole) and dioxane (5 ml) was stirred at room temperature for 14 hrs. The reaction mixture was concentrated in vacuo and dissolved with 18 ml of DMF-$H_2O$ (4:1). To this solution was added 393 mg (2.3 mmole) of benzylbromide and 18-crown-6 (24 mg, 0.096 mmole). The reaction mixture was stirred for 6 hrs., poured into water (60 ml) and extracted wtih ether for four times. The combined extracts were concentrated in vacuo and chromatographed in Silic CC-7[20 g; elution with ether:n-hexane(3:1)] to give 314 mg of the N-3-hydroxy-1-carboxypropyl-α-tetradropyranoxy-γ-butyrolactoaminobutyric acid benzyl ester as a colorless oil (Yield: 56%)(XI).

IR($CHCl_3$) 3540, 1740, 1695 cm$^{-1}$ $^1$H NMR($CDCl_3$) δ7.24(s, 5H), 7.22(s, 5H), 5.05(s, 4H).

Analysis-Calculated for $C_{32}H_{43}O_9N$(percent): C, 65.62; H, 7.40. Found: C, 65.68; H, 7.51.

To a suspension of PCC (681 mg, 3.16 mmole) in dry methylene chloride (5 ml) was added at room temperature under nitrogen a solution of the compound (370 mg, 0.632 mmole) in $CH_2Cl_2$ (2 ml). The reaction mixture was stirred for 2 hrs. and quenched by the addition of 30 ml of ether. Powdered magnesium sulfate (5 g) was added to suspend the reaction mixture. Filtration and concentration of above mixture gave the crude oil, which upon chromatography on Silic CC-7[50 g; elution with ether:n-hexane(2:3)] yielded 277 mg of one of the invention compounds (I) (R=H, R$^1$=tetrahdropyranyl, R$^2$=t-butoxycarbonyl, R$^3$=benzyl) as a colorless oil (Yield: 75%).

IR($CHCl_3$) 2725, 1743, 1735, 1695 cm$^{-1}$ $^1$H NMR($CDCl_3$) δ9.76(bs, 1H), 7.32(s, 5H), 7.28(s, 5H), 5.12(s, 4H), 4.28 4.68(m, 3H), 1.35(s, 9H).

Analysis-Calculated for $C_{32}H_{41}O_9N$(percent): C, 65.87; H, 7.14; N, 2.38.

EXAMPLE 2

On the above-mentioned coupling reaction with 3-formyl-2-tetrahydropyranoxypropionic acid benzyl ester, using α-amino-β-tetrahydropyranoxy-γ-butyrolactone trifluoroacetate instead of α-amino-γ-butyrolactone trifluoroacetate brings another compound of the invention compounds (I) (R=tetrahydropyranoxy, R$^1$=tetrahydropyranyl, R$^2$=t-butoxycarbonyl, R$^3$=benzyl), by the same manner mentioned above.

The synthesis of mugineic acids from these invention compounds is shown in the following references.

REFERENCE 1

To a solution of Benzyl azetizine-2-carboxylate trifluoroacetate (XIII) 46 mg, 0.15 mmole) in dry methanol (1 ml) at 0° C. under nitrogen was added a solution of the invention compound (I) (R=H, R$^1$=tetrahydropyranyl, R$^2$=t-butoxycarbonyl, R$^3$=benzyl) (50 mg, 0.19 mmole) in 1 ml of methanol and then, sodium cyanoborohydride (7.0 mg, 1.1 mmole). The reaction mixture was warmed to room temperature after 30 minutes and stirred for 16 hrs. The reaction mixture was poured into water and methanol was evaporated in vacuo. The resulting reaction mixture was extracted with chloroform (3 times) and the combined extracts were dried ($MgSO_4$) and concentrated to give the crude oil. Purification with column chromatography on silica gel [10 g; elution with ether:n-hexane(1:1)] to afford 41 mg of the protected 2'-deoxymugineic acid as a colorless oil (Yield: 59%).

IR($CHCl_3$) 1740, 1690 cm$^{-1}$ $^1$H NMR($CDCl_3$ at 50° C.) δ7.30(s, 10H), 7.27(s, 5H), 5.20(d, 1H, J=12 Hz), 5.11(s, 4H), 5.06(d, 1H, J=12 Hz), 1.35(s, 9H), Mass spectrum m/e 756(M$^+$ +1).

Analysis-Calculated for $C_{43}H_{54}O_{10}N_2$ (percent): C, 68.05; H, 7.17; N, 3.69. Found: C, 68.11; H, 7.18; N, 3.64.

A stirred suspension of the protected 2'-deoxymugineic acid (43 mg, 0.0567 mmole) and 5% Pd-C (6 mg) in ethanol-water (2 ml; 4:1) and trace amount of 1 N HCl (1 μl) was treated with hydrogen (1 atmosphere). The reaction mixture was stirred for 14 hrs. at room temperature, filtered and the filtrate was concentrated in vacuo affording 33 mg (100%) of the amorphous solid. The hydrogenated product (33 mg) was treated with trifluoroacetate acid (1 ml) for 30 minutes. The resulting trifluoroacetate after dilution with 10 ml of water was put onto Dowex-50Wx6 ion exchange resin (5 g) and eluted with 1 N aquous ammonia. The aquous solution was concentrated in vacuo yielded the crude 2'-deoxymugineic acid(III), which was chromatographed on Sephadex G-10 (30 g; elution with water) to give 18 mg of pure 2'-deoxymugineic acid as white crystals (Yield: 100%).

IR(KBr) 3450, 1715, 1610, 1395 cm$^{-1}$ $^1$H NMR($D_2O$) δ4.75(t, J=9.5Hz), 2.62(m), 4.04(m), 3.45(m), 2.17(m), 3.84(dd, J=4.8), M.P. 198.4°∼200.5° C. [α]$_D^≦$ −70.5°(C=1.08, $H_2O$), $C_{12}H_{20}O_7N_2$, m/e 286(M$^+$ +8).

REFERENCE 2

On the above mentioned reaction with benzyl azetizine-2-carboxylate trifluoroacetate, using another compound of the invention compounds cited Example 2 brings mugineic acid (II) by the same manner mentioned above.

IR(KBr) 3450, 3200, 1605 cm$^{-1}$ $^1$H NMR($D_2O$) δ2.88(m, 2H), 2.72(m, 2H), 3.36(m, 2H), 3.98(d, 1H, J=3.5 Hz), 4.17(m, 2H), 4.40 4.60(m,2H), 5.00(t, 1H, J=9Hz). M.P. 210°∼212° C. (decomp.) [α]$_D^≦$ −70.7°(C=0.97, $H_2O$).

Analysis-Calculated for (percent): C, 45.00; H, 6.29; N, 8.75. Found: C, 45.02; H, 6.32; N, 8.70. Mass spectrum m/e 321(M$^+$ +1).

REFERENCE 3

To stirred solution of α-amino-γ-butyrolactone trifluoroacetate (72 mg, 0.334 mmole) in dry methanol (2 ml) at 0° C. was added a solution of one of the invention compounds (R=H, R$^1$=tetrahydropyranyl, R$^2$=t-butoxycarbonyl, R$^3$=benzyl) (135 mg, 0.223 mmole) in dry methanol (1.5 ml) followed by sodium cyanoborohydride (14.3 mg, 0.223 mmole). The reaction mixture was stirred at 0° C. for 1 hr. and room temperature, 16 hrs. The reaction was quenched by the addition with water (5 ml). Methanol was distilled in vacuo and the resultant mixture was extracted with chloroform (3 times). The combined extracts were dried over with magnesium sulfate, concentrated in vacuo and chromatographed on Silic CC-7 [20 g; elution with ether:n-hexane (4:1)] to give 132 mg of the homoserine lactone derivatives (XV) (R$^1$=tetrahydropyranyl, R$^2$=t-butoxycarbonyl, R$^3$=benzyl) as a colorless oil (Yield: 88%).

IR($CHCl_3$) 1775, 1740, 1690 cm$^{-1}$ $^1$H NMR($CDCl_3$) δ7.32(s, 5H), 7.30(s, 5H), 5.14(s, 2H), 5.12(s, 2H), 1.40(s, 9H).

Analysis-Calculated for $C_{36}H_{48}O_{10}N_2$(percent): C, 64.65; H, 7.23; N, 4.19. Found: C, 64.51; H, 7.33; N, 4.11.

The deprotection of carboxyl, imino and hydroxy groups brings avenic acid A lactone derivatives, which is hydrolyzed to give avenic acid A (IV).

$^1$H NMR(NaOD) δ3.93(dd, 1H, J=4.1, 7.8 Hz), 3.48(t, 2H, J=7.1 Hz), 2.98(t, 1H, J=6.8 Hz), 2.93(dd, 1H, J=6.0, 7.7 Hz), 2.52(m, 1H), 2.30 2.45(m, 3H), 1.59 1.80(m, 5H), 1.48 1.59(m, 1H).

What is claimed is:

1. Homoserine aldehyde derivatives represented by the formula (I)

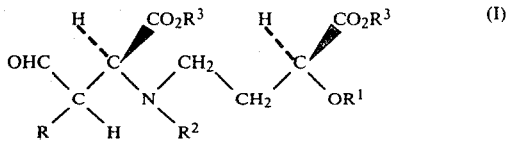

wherein R is hydrogen or hydroxy, $R^1$ is selected from a group consisting of tetrahydropyranyl, methoxymethylene, methoxyethoxymethylene, 1-ethoxyethyl, t-butyl, dimethyl-t-butylsilyl, acetyl, trifluoroacetyl, triphenylmethyl or diphenylmethyl, $R^2$ is selected from a group consisting of t-butoxycarbonyl, benzyloxycarbonyl, trifluoroacetyl or formyl and $R^3$ is selected from a group consisting of benzyl, p-methoxybenzyl, methyl, ethyl, or diphenylmethyl.

* * * * *